(12) United States Patent
Lieber et al.

(10) Patent No.: US 7,976,537 B2
(45) Date of Patent: *Jul. 12, 2011

(54) OPTICAL PYROMETRIC CATHETER FOR TISSUE TEMPERATURE MONITORING DURING CARDIAC ABLATION

(75) Inventors: Chad Allen Lieber, Chino Hills, CA (US); Shiva Sharareh, Laguna Niguel, CA (US)

(73) Assignee: Biosense Webster, Inc., Diamond Bar, CA (US)

( * ) Notice: Subject to any disclaimer, the term of this patent is extended or adjusted under 35 U.S.C. 154(b) by 282 days.

This patent is subject to a terminal disclaimer.

(21) Appl. No.: 11/770,604

(22) Filed: Jun. 28, 2007

(65) Prior Publication Data

US 2009/0005771 A1 Jan. 1, 2009

(51) Int. Cl.
*A61B 18/18* (2006.01)

(52) U.S. Cl. .............................. 606/15; 606/13; 606/41
(58) Field of Classification Search .................. None
See application file for complete search history.

(56) References Cited

U.S. PATENT DOCUMENTS

| | | | |
|---|---|---|---|
| 4,679,934 A * | 7/1987 | Ganguly et al. ................. 356/43 |
| 5,354,323 A * | 10/1994 | Whitebook ..................... 607/89 |
| 5,391,199 A | 2/1995 | Ben-Haim | |
| 5,443,489 A | 8/1995 | Ben-Haim | |
| 5,456,662 A * | 10/1995 | Edwards et al. ................. 604/22 |
| 5,480,422 A | 1/1996 | Ben-Haim | |
| 5,486,161 A * | 1/1996 | Lax et al. ......................... 604/22 |
| 5,546,951 A | 8/1996 | Ben-Haim | |
| 5,558,091 A | 9/1996 | Acker et al. | |
| 5,568,809 A | 10/1996 | Ben-Haim | |
| 5,709,473 A * | 1/1998 | Sultan et al. ................... 374/131 |
| 5,782,760 A * | 7/1998 | Schaer ........................... 600/381 |
| 5,964,757 A | 10/1999 | Ponzi | |
| 6,405,078 B1 * | 6/2002 | Moaddeb et al. ............... 604/21 |

(Continued)

FOREIGN PATENT DOCUMENTS

WO   WO 95/02995   2/1995

(Continued)

OTHER PUBLICATIONS

International Search Report dated Sep. 11, 2008 for International application No. EP 08/25/2237, 6 sheets, indicating relevance of corresponding references in this IDS.

(Continued)

*Primary Examiner* — Henry M Johnson, III
*Assistant Examiner* — Lynsey Crandall
(74) *Attorney, Agent, or Firm* — Christie, Parker & Hale, LLC

(57) ABSTRACT

A system for opto-pyrometric tissue temperature monitoring in real time. The system is adapted for cardiac ablation and tissue temperature measurement, having a catheter having a tip electrode adapted for RF ablation of cardiac tissue and an optical collector whose distal end is received in an opening formed in the tip electrode to detect black body radiation from the cardiac tissue. The system includes an optical detection system in communication with the optical collector, the optical processing system processing signals representative of a wavelength of at least a portion of the black body radiation to determine a tissue temperature. The incorporation of an optical collector within a catheter tip permits real time monitoring of tissue temperature during ablation and lesion formation to prevent critical thresholds in temperature associated with events that can damage tissue, including steam pop, thrombus, char, etc.

18 Claims, 15 Drawing Sheets

U.S. PATENT DOCUMENTS

| | | | |
|---|---|---|---|
| 6,468,260 B1 | 10/2002 | Bumbalough et al. | |
| 6,592,580 B1 | 7/2003 | Stockert | |
| 6,602,242 B1 | 8/2003 | Fung et al. | |
| 7,077,842 B1 * | 7/2006 | Cosman | 606/41 |
| 2002/0161362 A1 * | 10/2002 | Penny et al. | 606/41 |
| 2003/0065315 A1 * | 4/2003 | Hareyama et al. | 606/11 |
| 2003/0216720 A1 * | 11/2003 | Sinofsky | 606/11 |
| 2005/0131400 A1 * | 6/2005 | Hennings et al. | 606/15 |
| 2006/0122587 A1 | 6/2006 | Sharareh | |
| 2006/0173449 A1 | 8/2006 | Sharareh et al. | |
| 2006/0264925 A1 | 11/2006 | Sharareh et al. | |
| 2007/0066972 A1 | 3/2007 | Ormsby et al. | |

FOREIGN PATENT DOCUMENTS

| | | |
|---|---|---|
| WO | WO 02/38065 A1 | 5/2002 |
| WO | WO 2006/127241 | 11/2006 |
| WO | WO 2007/146995 | 12/2007 |

OTHER PUBLICATIONS

International Search Report dated Nov. 27, 2008 for International application No. EP 08/25/2234, 6 sheets, indicating relevance of corresponding references in this IDS.

U.S. Appl. No. 11/281,853, filed Nov. 17, 2005, Sharareh et al.

* cited by examiner

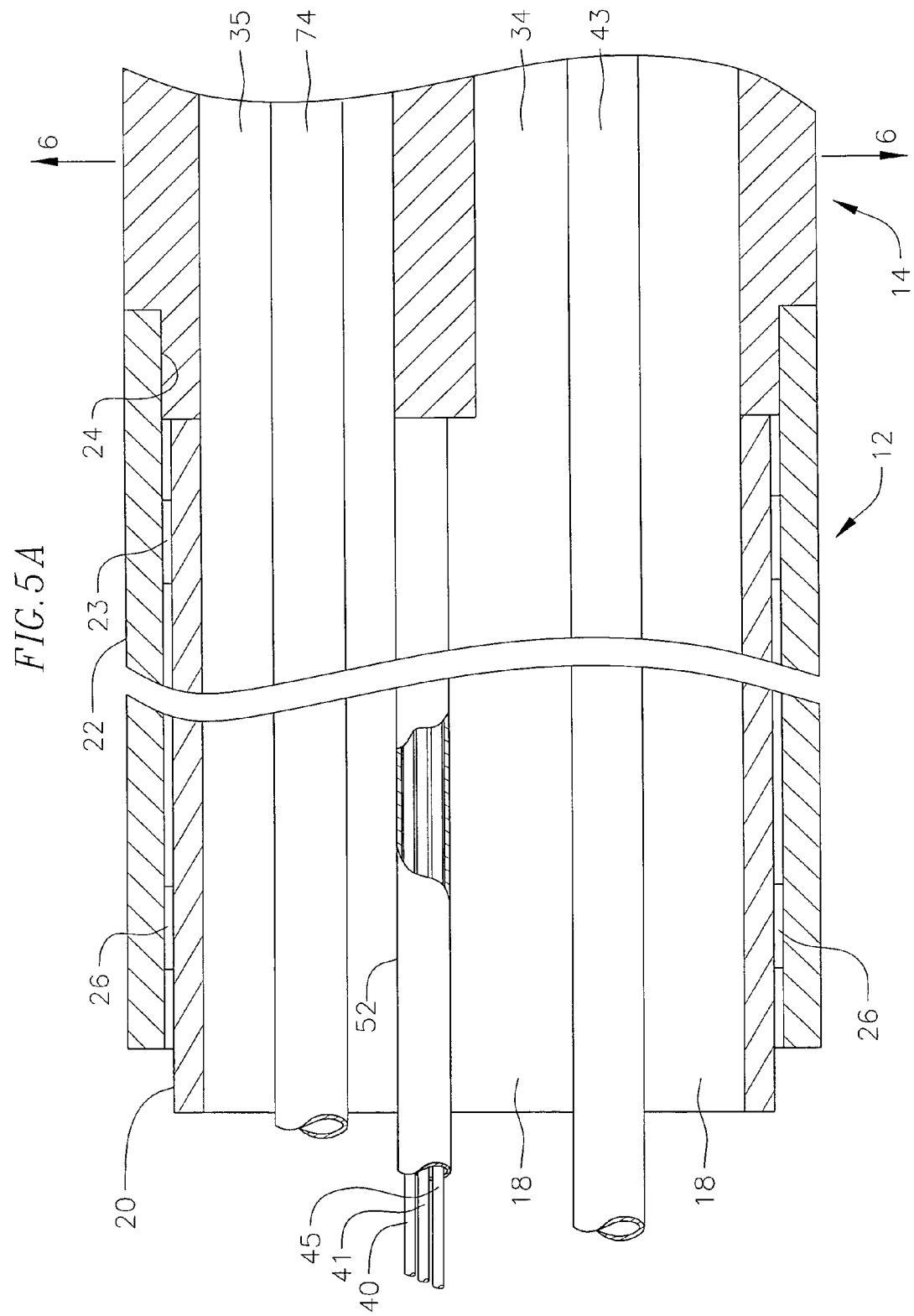

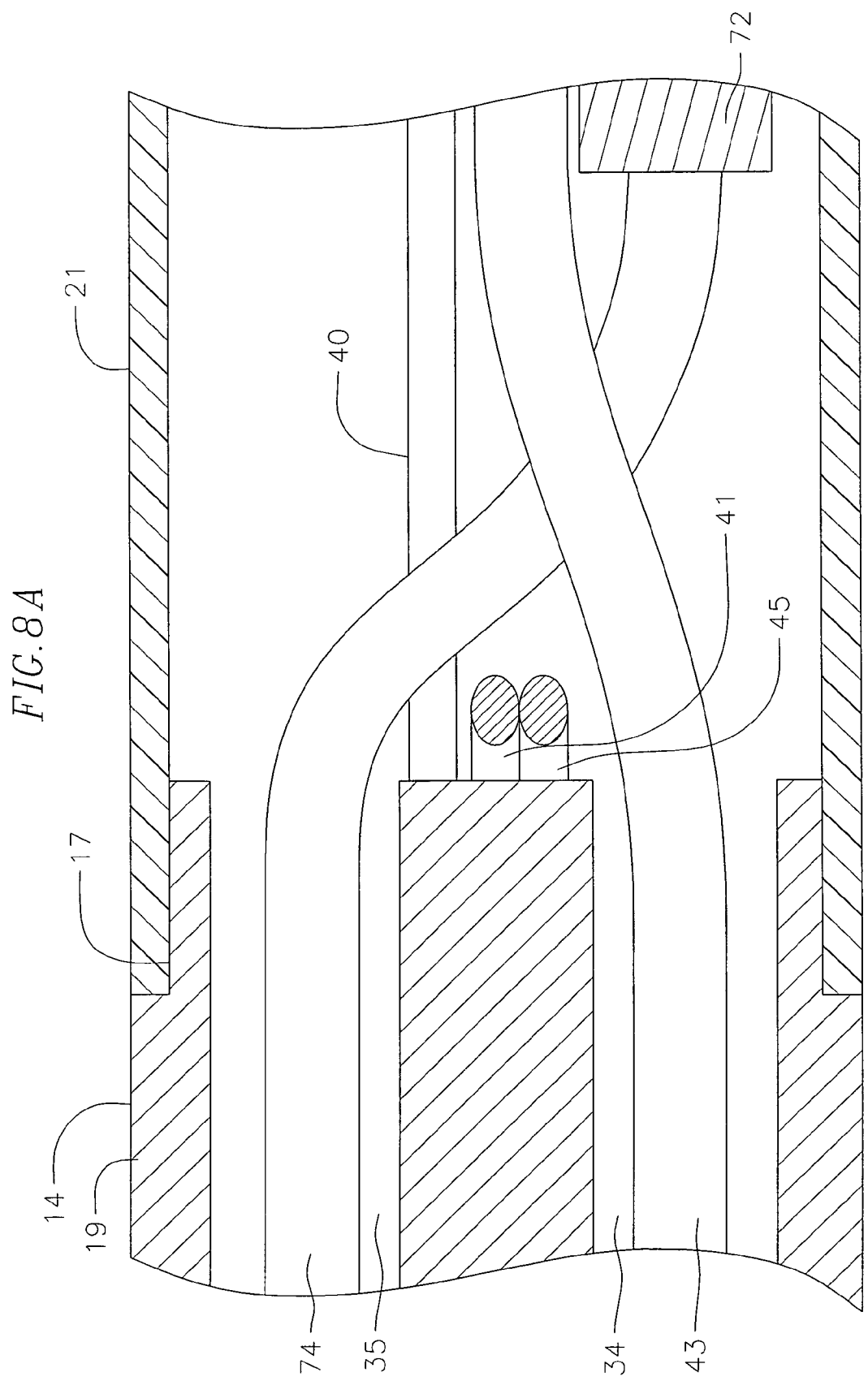

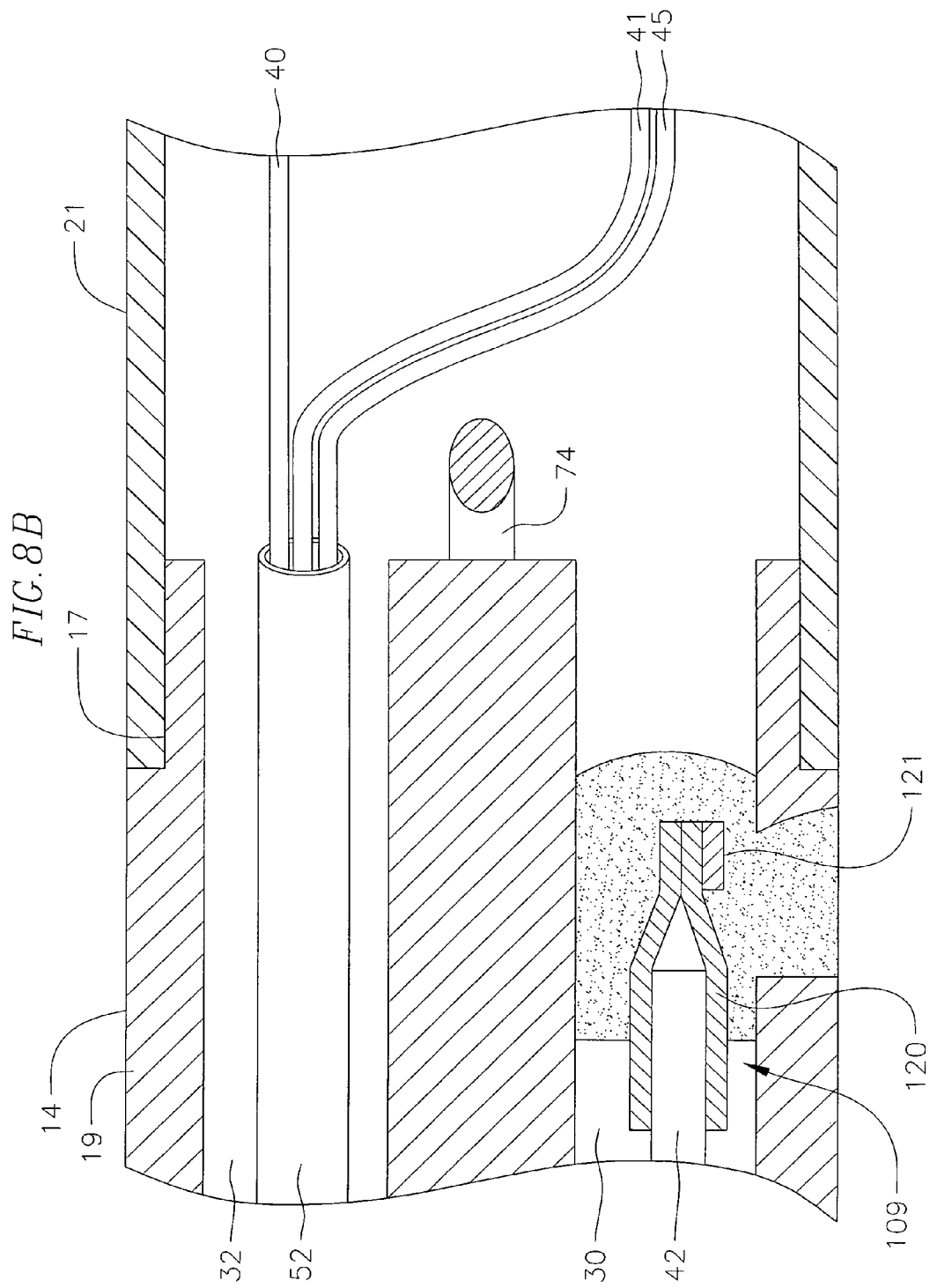

OPTICAL PYROMETRIC CATHETER FOR TISSUE TEMPERATURE MONITORING DURING CARDIAC ABLATION

FIELD OF INVENTION

The present invention relates to electrophysiologic catheters, and in particular to optical pyrometric electrophysiologic catheters for monitoring tissue temperature.

BACKGROUND

For certain types of minimally invasive medical procedures, real time information regarding the condition of the treatment site within the body is unavailable. This lack of information inhibits the clinician when employing catheter to perform a procedure. An example of such procedures is tumor and disease treatment in the liver and prostate. Yet another example of such a procedure is surgical ablation used to treat atrial fibrillation. This condition in the heart causes abnormal electrical signals, known as cardiac arrhythmias, to be generated in the endocardial tissue resulting in irregular beating of the heart.

The most frequent cause of cardiac arrhythmias is an abnormal routing of electricity through the cardiac tissue. In general, most arrhythmias are treated by ablating suspected centers of this electrical misfiring, thereby causing these centers to become inactive. Successful treatment, then, depends on the location of the ablation within the heart as well as the lesion itself. For example, when treating atrial fibrillation, an ablation catheter is maneuvered into the right or left atrium where it is used to create ablation lesions in the heart. These lesions are intended to stop the irregular beating of the heart by creating non-conductive barriers between regions of the atria that halt passage through the heart of the abnormal electrical activity.

The lesion should be created such that electrical conductivity is halted in the localized region (transmurality), but care should be taken to prevent ablating adjacent tissues. Moreover, because the ablation process can raise tissue temperature due to resistive heating, excessive heating of the tissue can cause undesirable charring and localized coagulation, and even evaporate water in the blood and tissue leading to steam pops which can damage tissue.

Thus, it would be desirable to provide an electrophysiologic catheter that permits real time monitoring of tissue temperature during ablation and lesion formation to prevent, or at least minimize, critical thresholds in temperature associated with such events as steam pop, thrombus formation, char, etc. Because all tissues emit black body radiation that is directly related to temperature, it would be desirable for an electrophysiologic catheter to detect black body radiation for noninvasive temperature determination.

A black body radiation curve such as in FIG. 1 shows that the black body radiates energy at every wavelength (the curve approaches the x-axis but never touches it). The black body has a wavelength at which most of the radiant energy is emitted, and in FIG. 1, the peak wavelength is about 500 nm for a temperature of 5000K. This peak wavelength, along with the radiation curve, however varies with temperature, as shown in FIG. 2. In particular, as the temperature increases, the peak wavelength decreases, as well as the standard amount of energy emitted by the black body, as represented by the area under each curve.

Black body laws can be applied to many thing, including the human body. Much of a person's energy is lost in the form of electromagnetic radiation, of which most is infrared. A human body has a temperature is about 36.5 C (98.6 F or 310 K) and infrared (IR) radiation is of a wavelength longer than that of visible light but shorter than that of radio waves. Infrared radiation spans three orders of magnitude and has wavelengths between approximately 750 nm and 1 mm. As such, the peak wavelength for human tissue may range between about 2000 nm and 4000 nm, preferably between about 2000 nm and 3100 nm, and more preferably between about 2000 nm and 3000 nm.

Therefore, by monitoring the peak wavelength or peak wavelength region(s) of the black body radiation of tissue, the temperature of the tissue can be obtained in real time as a means of preventing overheating of tissue during ablation and lesion formation.

SUMMARY OF THE INVENTION

The present invention is directed to a system for optopyrometric tissue temperature monitoring in real time. Black body radiation is a physical effect directly related to temperature. This radiation can be measured via optical instruments noninvasively to determine the temperature of an object. Because the radiation is optical, it can be measured by an optical collector, for example, an optical fiber. Accordingly, the incorporation of an optical collector within a catheter tip permits real time monitoring of tissue temperature during ablation and lesion formation to prevent critical thresholds in temperature associated with events that can damage tissue, including steam pop, thrombus, char, etc.

Advantageously, the present invention has a relative simplistic design which allows the temperature sensor, e.g., the optical fiber, to be used in a variety of catheter configurations, including needle ablation and injection catheter, irrigated and nonirrigated catheters, as well as a multitude of catheter curve shapes. And, because long wavelengths associated with black body radiation transmit readily through cardiac tissue, the present invention is able to collect an integrative temperature of an acceptance cone of the optical collector optical fiber. Accordingly, temperature measurement is possible not just at the surface of the tissue, but at depths up to several millimeters or more, depending on the wavelength range utilized.

In one embodiment of the present invention, a system for detecting black body radiation during cardiac ablation has a catheter, an ablation energy source and an optical detector. The catheter has an ablation element and an optical collector adapted to collect black body radiation from tissue. The ablation energy source is adapted to deliver ablation energy to the ablation element. The optical detector adapted to detect the black body radiation at a selected wavelength region.

In another embodiment of the present invention, a system for ablation and tissue temperature measurement has a catheter and an optical detection system. The catheter has an ablation element and an optical collector adapted to collect black body radiation from ablated tissue. The optical detection system has a wavelength selector and a quantification apparatus to provide signals representative of a wavelength region of the black body radiation. A processor is provided to determine a temperature measurement from the signals. In a more detailed embodiment, the optical collector includes an optical fiber, wherein the temperature measurement is integrative over an acceptance cone of the optical fiber. Moreover, the tissue of interest is cardiac tissue and catheter is adapted for ablation by radio frequency (RF) and other energy sources, as well, including microwave, ultrasound, laser, cryoablation.

In a more detailed embodiment of the present invention, a system for cardiac ablation and tissue temperature measurement includes a catheter and an optical detection system, wherein the catheter has a catheter body, a deflectable portion distal the catheter body, and a tip section, the tip section having a tip electrode adapted for RF ablation of cardiac tissue and an optical collector whose distal end is received in an opening formed in the tip electrode to detect black body radiation from the cardiac tissue, and wherein the optical detection system is in communication with the optical collector, the optical detection system processing signals representative of a wavelength of at least a portion of the black body radiation to determine a tissue temperature. The detection system can include a wavelength selector, a quantification apparatus to provide the signals and a processor to determine the tissue temperature based on the signals.

In one embodiment, a catheter suitable for use with the system has a catheter body, a deflectable portion distal the catheter body, and a tip section having a tip electrode adapted for RF ablation of cardiac tissue and an optical collector adapted to detect black body radiation indicative of a temperature of the cardiac tissue. The optical collector can be an optical fiber, wherein the tip section houses a distal end of the optical fiber. Moreover, the catheter can include a control handle, wherein the optical fiber extends through the catheter from the tip section to the control handle proximal the catheter body. The catheter can also be configured for irrigation. The tip electrode can include a shell and a plug, where the optical fiber extends through the plug and toward a distal end of the shell. The catheter can further house an electromagnetic location sensor.

BRIEF DESCRIPTION OF THE DRAWINGS

These and other features and advantages of the present invention will be better understood by reference to the following detailed description when considered in conjunction with the accompanying drawings wherein:

FIG. 5A is a side cross-sectional view of an embodiment of a catheter according to the present invention, including the junction between a catheter body and an intermediate section, taken along a first diameter.

FIG. 8A is a side cross-sectional view of an embodiment of a catheter according to the invention, including the junction between an intermediate section and a plastic housing, taken along a first diameter.

FIG. 8B is a side cross-sectional view of an embodiment of a catheter according to the invention, including the junction between an intermediate section and a plastic housing, taken along a second diameter generally perpendicular to the first diameter of FIG. 8A.

DETAILED DESCRIPTION OF THE INVENTION

Figure 3:
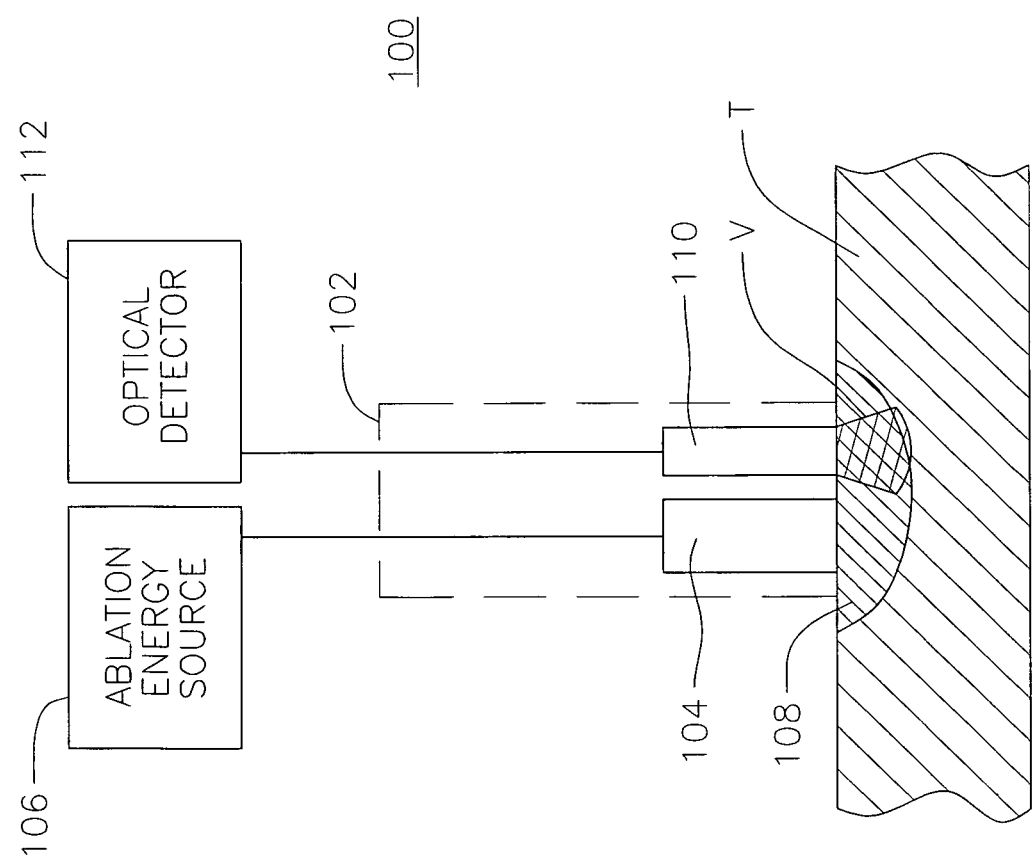
FIG. 3 illustrates an embodiment of a system for ablation and optical pyrometry in accordance with the present invention.

FIG. 3 illustrates an embodiment of a system 100 for optical pyrometric temperature monitoring of tissue subject to ablation. Cardiac tissue T is undergoing RF ablation by a catheter 102 having an ablation element 104 that is energized by an ablation energy source 106 to form lesion 108. In accordance with the present invention, the catheter is also adapted to collect optical data, including black body radiation, from the tissue to obtain a temperature of the tissue and lesion. In particular, the catheter includes an optical collection apparatus 110 which collects the black body radiation from the lesion for delivery to an optical detector 112 that quantifies the amount of black body radiation emitted at a particular wavelength region(s). As understood by one of ordinary skill in the art, the black body radiation of the tissue is an effect directly related to the temperature of the tissue. And, by enabling real time monitoring of tissue temperature within a volume V extending a predetermined depth into the tissue, the system 100 can facilitate the prevention of critical thresholds in temperature associated with such events as steam pop, thrombus formation, char, and the like. In a more detailed embodiment of FIG. 4, a catheter-based system 120 for real-time optical pyrometric temperature monitoring is illustrated. Endo- or epi-cardiac tissue T is subjected to RF ablation by a catheter 10 having a deflectable (uni or bi-directional) intermediate section 14 and a distal tip section 36 adapted for RF ablation in creating a lesion 17. The tip section 36 is also equipped with an optical collection apparatus, including a wave guide in the form of a fiber optic (or optical fiber, used interchangeably herein) 43, or other form of light pipe or a hollow wave guide, to collect black body radiation from the ablated tissue and communicate, relay, transport and/or deliver same to an optical detection system 130. The system 130 comprises at least one wavelength selective element 131 that includes optics 132, as are known in the art, for example, a system of lenses, mirrors and/or prisms, for receiving black body radiation data 134 from the optic fiber 43, and a spectrometer or other electromagnetic radiation splitting device into desired components 136 that are transmitted into a quantification apparatus 140 that quantifies the amount of black body radiation emitted at a particular wavelengths.

The quantification apparatus 140 translates measured light intensities into an electrical signal that can be processed with a computer 142 and displayed graphically to an operator of the catheter 10. The quantification apparatus 140 may comprise a charged coupled device (CCD) for simultaneous detection and quantification of these light intensities. Alternatively, a number of different light sensors, including photodiodes, photomultipliers or complementary metal oxide semiconductor (CMOS) detectors may be used in place of the CCD converter. Information is transmitted from the quantification device 140 to the computer 142 where a graphical display or other information is generated regarding temperature of the lesion. An optical detection system adaptable for use with the present invention is described in U.S. application Ser. No. 11/281,179 entitled Apparatus for Real Time Evaluation of Tissue Ablation, and Ser. No. 11/281,853 entitled Method for Real Time Evaluation of Tissue Ablation, the entire disclosures of which are hereby incorporated by reference.

Thus, in accordance with the present invention, the system can obtain tissue temperature extending from the surface down to a depth in an integrated measurement. In particular, the present system can yield an integrative temperature of tissue over a radiation acceptance cone C of the fiber optic. Accordingly, temperature measurement is possible not just at the surface of the tissue, but at depths up to several millimeters or more, depending on the wavelength range utilized. Such depths may range between about 0 mm and 5 mm, and preferably about 1.0 mm and 3.0 mm. A diameter of the acceptance cone C is further adjustable by varying the numerical aperture of the collecting fiber optic 19.

The catheter 10 itself comprises an elongated catheter body 12 having proximal and distal ends, a deflectable intermediate section 14 at the distal end of the catheter body 12, and a tip section 36 at the distal end of the intermediate section, and a control handle 16 at the proximal end of the catheter body 12. With additional reference to FIGS. 5A and 5B, the catheter body 12 comprises an elongated tubular construction having a single, axial or central lumen 18. The catheter body 12 is flexible, i.e., bendable, but substantially non-compressible along its length. The catheter body 12 can be of any suitable construction and made of any suitable material. A construction comprises an outer wall 22 made of an extruded plastic. The outer wall 22 may comprise an imbedded braided mesh of stainless steel or the like to increase torsional stiffness of the catheter body 12 so that, when the control handle 16 is rotated, the catheter body 12, the intermediate section 14 and the tip section 36 of the catheter 10 will rotate in a corresponding manner.

Extending through the single lumen 18 of the catheter body 12 are components, for example, wires, tubes, fiber optics and/or cables. A single lumen catheter body can be preferred over a multi-lumen body because it has been found that the single lumen body permits better tip control when rotating the catheter. The single lumen permits the various components to float freely within the catheter body. If such wires, tube, optics and cables were restricted within multiple lumens, they tend to build up energy when the handle is rotated, resulting in the catheter body having a tendency to rotate back if, for example, the handle is released, or if bent around a curve, to flip over, either of which are undesirable performance characteristics.

The outer diameter of the catheter body 12 is not critical, but is preferably no more than about 8 french, more preferably 7 french. Likewise the thickness of the outer wall 22 is not critical, but is thin enough so that the central lumen 18 can accommodate the aforementioned components. The inner surface of the outer wall 22 may be lined with a stiffening tube 20, which can be made of any suitable material, such as polyimide or nylon. The stiffening tube 20, along with the braided outer wall 22, provides improved torsional stability while at the same time minimizing the wall thickness of the catheter, thus maximizing the diameter of the central lumen 18. The outer diameter of the stiffening tube 20 is about the same as or slightly smaller than the inner diameter of the outer wall 22. Polyimide tubing may be preferred for the stiffening tube 20 because it may be very thin walled while still providing very good stiffness. This maximizes the diameter of the central lumen 18 without sacrificing strength and stiffness.

The catheter body 12 may have an outer wall 22 with an outer diameter of from about 0.090 inch to about 0.098 inch and an inner diameter of from about 0.061 inch to about 0.078 inch and a polyimide stiffening tube 20 having an outer diameter of from about 0.060 inch to about 0.077 inch and an inner diameter of from about 0.051 inch to about 0.069 inch.

Figure 5B:
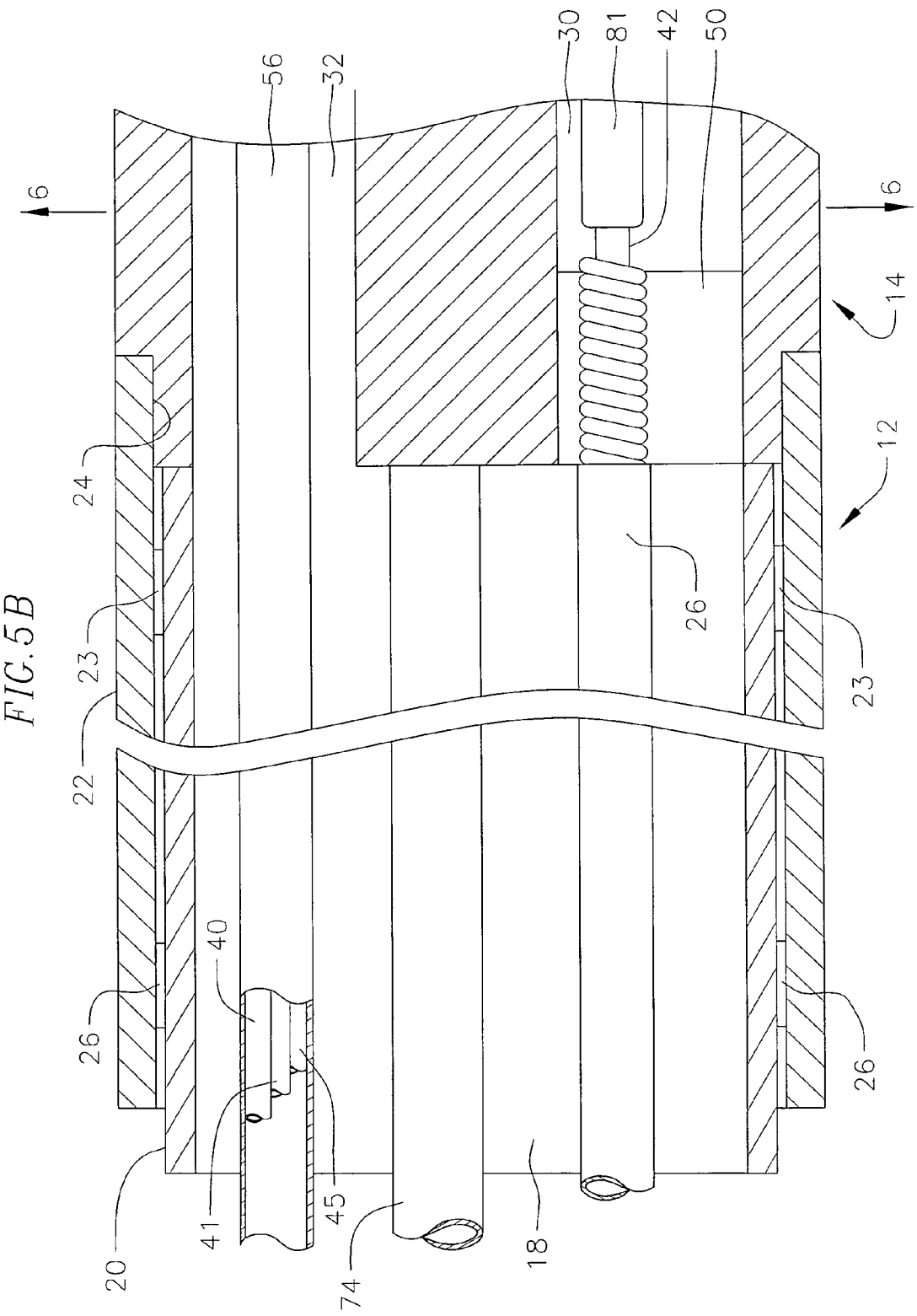
FIG. 5B is a side cross-sectional view of an embodiment of a catheter according to the invention, including the junction between a catheter body and an intermediate section, taken along a second diameter generally perpendicular to the first diameter of FIG. 5A.

As shown in the embodiments of FIGS. 5A and 5B, the distal end of the catheter body 12 that may be attached to the intermediate section 14 by means of a notch 24 formed in the proximal end of the intermediate section 14 that receives the inner surface of the outer wall 22 of the catheter body 12. The intermediate section 14 and catheter body 12 are attached by glue or the like. Before the intermediate section 14 and catheter body 12 are attached, the stiffening tube 20 is inserted into the catheter body 12. The distal end of the stiffening tube 20 is fixedly attached near the distal end of the catheter body 12 by forming a glue joint 23 with polyurethane glue or the like. Preferably a small distance, e.g., about 3 mm, is provided between the distal end of the catheter body 12 and the distal end of the stiffening tube 20 to permit room for the catheter body 12 to receive the notch 24 of the intermediate section 14. If no compression coil is used, a force is applied to the proximal end of the stiffening tube 20, and, while the stiffening tube 20 is under compression, a first glue joint (not shown) is made between the stiffening tube 20 and the outer wall 22 by a fast drying glue, e.g. cyanoacrylate. Thereafter, a second glue joint 26 is formed between the proximal ends of the stiffening tube 20 and outer wall 22 using a slower drying but stronger glue, e.g., polyurethane.

If desired, a spacer can be located within the catheter body between the distal end of the stiffening tube and the proximal end of the tip section. The spacer provides a transition in flexibility at the junction of the catheter body and intermediate section, which allows this junction to bend smoothly without folding or kinking. A catheter having such a spacer is described in U.S. patent application Ser. No. 08/924,616, entitled "Steerable Direct Myocardial Revascularization Catheter", the entire disclosure of which is incorporated herein by reference.

Figure 6:
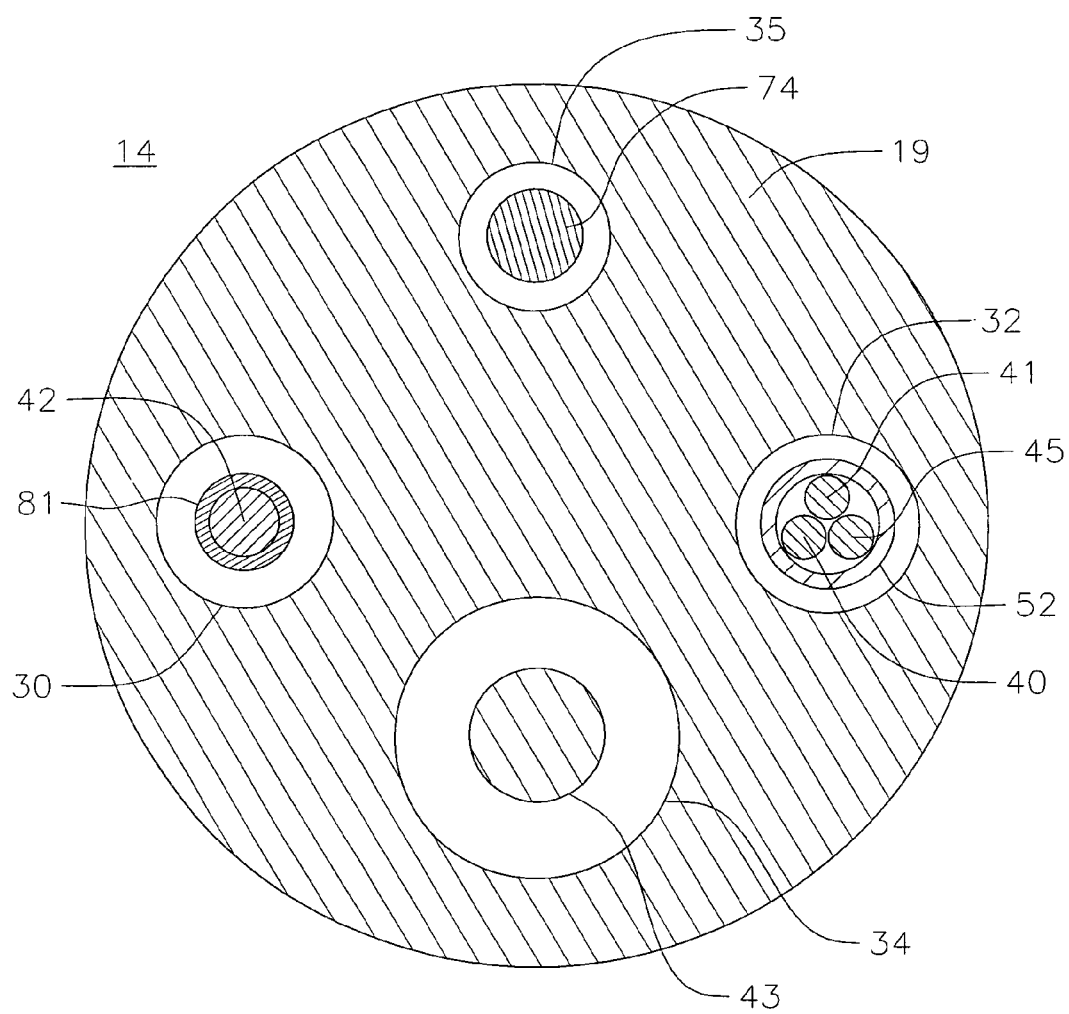
FIG. 6 is a longitudinal cross-sectional view of an embodiment of the intermediate section of FIGS. 5A and 5B, taken along line 6-6.

Referring also to FIG. 6, the intermediate section 14 distal the catheter body 12 comprises a shorter section of tubing 19 having multiple lumens. The tubing 19 is made of a suitable non-toxic material that is preferably more flexible than the catheter body 12. A suitable material for the tubing 19 is braided or non-braided polyurethane. The outer diameter of the intermediate section 14, like that of the catheter body 12, is preferably no greater than about 8 french, more preferably 7 french. The size and number of the lumens are not critical. In an embodiment, the intermediate section 14 has an outer diameter of about 7 french (0.092 inch). The tubing 19 is multi-lumened, for example, with a first lumen 30, a second lumen 32, a third lumen 34 and a fourth lumen 35. In the illustrated embodiment, the lumens 30, 32 and 35 all have approximately the same diameter of about 0.22 inch, whereas the lumen 34 has a larger diameter of about 0.44 inch.

Figure 7A:
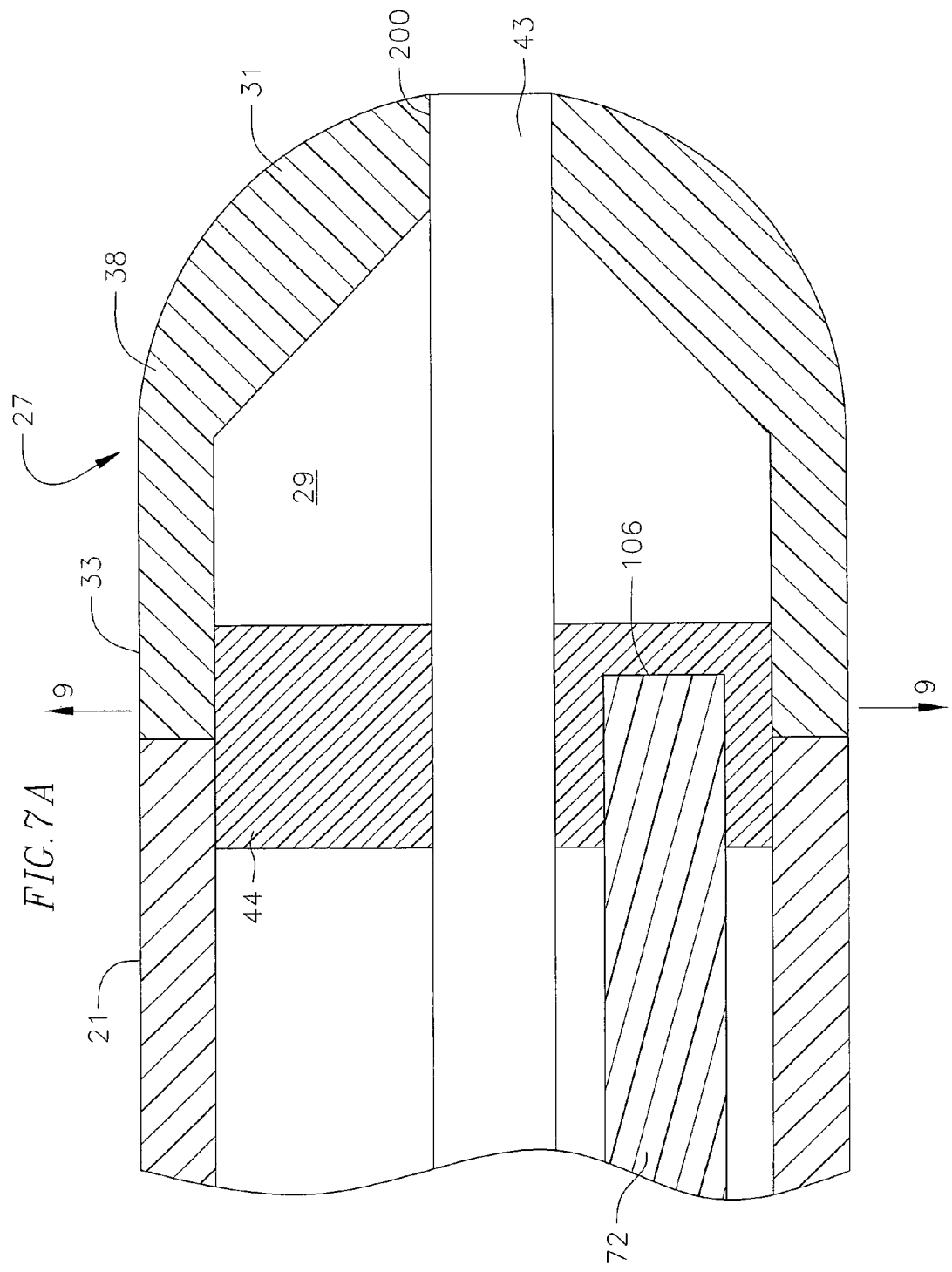
FIG. 7A is a side cross sectional view of an embodiment of a catheter according to the invention, including a junction between a plastic housing and a tip electrode, taken along a first diameter.
Figure 7B:
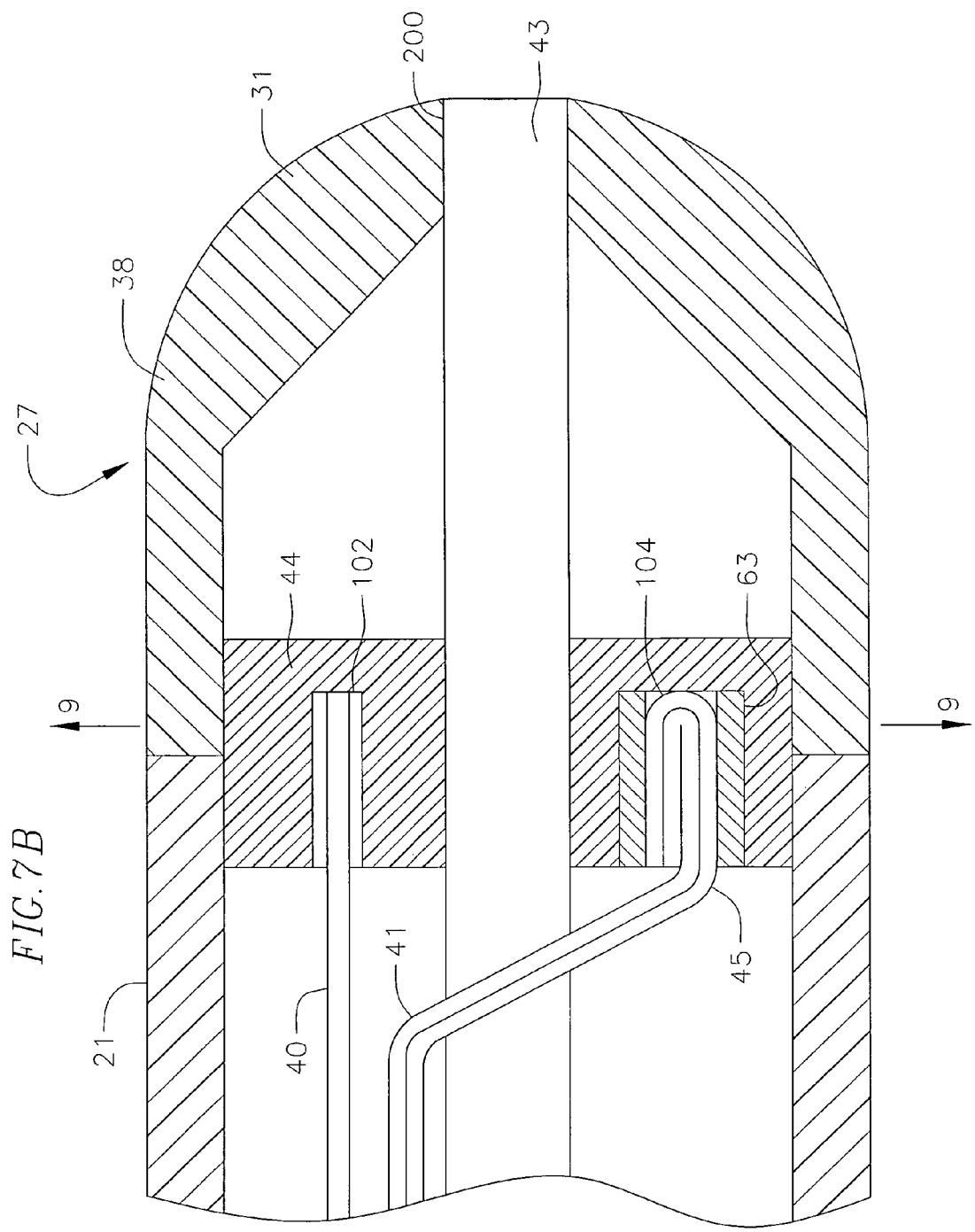
FIG. 7B is a side cross-sectional view of an embodiment of a catheter according to the invention, including a junction between a plastic housing and a tip electrode, taken near a second diameter generally perpendicular to the first diameter of FIG. 7A.

Extending from the distal end of the intermediate section 14 is the tip section 36 that includes a tip electrode 27 and a plastic housing 21, as shown in FIGS. 7A and 7B. The plastic housing 21, as also shown in FIGS. 8A and 8B, extends between and connects the tip electrode 27 and the tubing 19, and provides housing and/or transitional space for the components that extend into or through its lumen, as discussed further below. The plastic housing 21 is preferably made of polyetheretherketone (PEEK) and may be about 1 cm long. Its proximal end receives the outer circumferentially notched surface 17 of the tubing 19 of the intermediate section 14. The intermediate section 14 and the plastic housing 21 are attached by glue or the like. Components such as wires, cables and tubes that extend between the intermediate section 14 and the tip electrode 27 help keep the tip electrode in place.

In accordance with the present invention, the tip electrode 27 is adapted to ablate and collect black body radiation to monitor tissue temperature. As shown in FIGS. 7A and 7B, the tip electrode comprises a shell wall 38 and a plug 44. The shell 38 is configured with a distal dome end 31 and an open proximal portion 33 in communication with a hollow cavity 29. The distal dome end 31 of the shell is atraumatic and adapted for contact with tissue. The open proximal end 33 is configured to receive the plug 44 which, among other functions, stabilizes the optical fiber 43 extending into the distal end of the shell. The shell 38 and the plug 44 are formed from any suitable material that is opaque and/or reflective, and both thermally and electrically conductive which allows for radio frequency ablation using an RF generator. Such suitable materials include, without limitation, platinum-irridium, platinum, gold alloy, or palladium alloy.

Formed of the same or comparable material as the shell 38, the plug 44 has a generally elongated cylindrical configuration having a predetermined length, and a generally circular cross-section that matches the cross-section of the open proximal end 33 of the tip electrode 27. A distal portion of the plug 44 is press fitted, or fixed with solder into the open proximal end 33 to seal the hollow cavity 29, while a proximal portion of the plug 44 extends proximally from the tip electrode 27 for attachment to the housing 21.

The shell wall 38 has at least one opening for the tip electrode to receive a distal end of the optical fiber 43. The tip electrode can have any corresponding number of openings and optical fibers as desired or appropriate, although the number is dependent in part on the size of the tip electrode and the size and number of optical fibers housed therein. In the illustrated embodiment, the shell wall has a single collection opening 200 at the distal end that is on-axis along the longitudinal axis of the tip electrode.

In accordance with the present invention, blind holes and passages are provided in the plug 44 to allow components extending from the intermediate section 14 to be anchored to the plug or to pass through. In the illustrated embodiment of FIGS. 7A, 7B and 9, there are blind holes 102, 104 and 106 formed in the proximal surface of the plug in which distal ends of a lead wire 40, thermocouple wires 41 and 45 and a location sensor 72 are anchored, respectively. There is also a passage 108 through which the fiber optic cable 43 extends to the distal end of the tip electrode. The portions of the components extending through the passages in the plug 44 are securely fixed in the passages to the plug 44 by glue, adhesive or the like. As such, the passages and the plug help align, stabilize and secure the various components extending through the plug 44. In particular, the passage 108 helps minimize stress on the cable 43 in its transition between the intermediate section 14 and the tip electrode 27.

In operation, black body radiation from the tissue and lesion is collected by the catheter by means of the fiber optic cable 43 whose distal end is in communication with the outside of the tip electrode through the opening 200. The radiation is relayed from the distal end of the catheter by the fiber optic cable 43 which extends from the opening 200, through a passage 201 in the plug 44, the lumen of the plastic housing 21, the lumen 34 of the intermediate section 14, the central lumen of the catheter body 12, the control handle 16, out its proximal end where the radiation is further relayed to the optical detection system. The cable 43 has a coating to optically isolate itself along its length between the opening 200 and the optical detection system. The coating can be an opaque but reflective buffer material, e.g., aluminum, gold and the like, so that light cannot penetrate the side wall of the fiber 43.

It is understood by one of ordinary skill in the art that optical waveguides and fiber optic cables in general serve to communicate optical energy from one end to the other end, although these are not exclusive. It is understood that the fiber optic cable 43 may be any suitable optical wave guide wherein light introduced at one of the cable is guided to the other end of the cable with minimal loss. The cable 43 may be a single fiber optic cable or fiber bundles. It may be single mode (also known as mono-mode or uni-mode), multi-mode (with step index or graded index) or plastic optical fiber (POF), depending on a variety of factors, including but not limited to transmission rate, bandwidth of transmission, spectral width of transmission, distance of transmission, diameter of cable, cost, optical signal distortion tolerance and signal attenuation, etc. Moreover, light collection and delivery may be accomplished with other devices, such as air-core fibers, hollow waveguides, liquid waveguides and the like.

Figure 1:
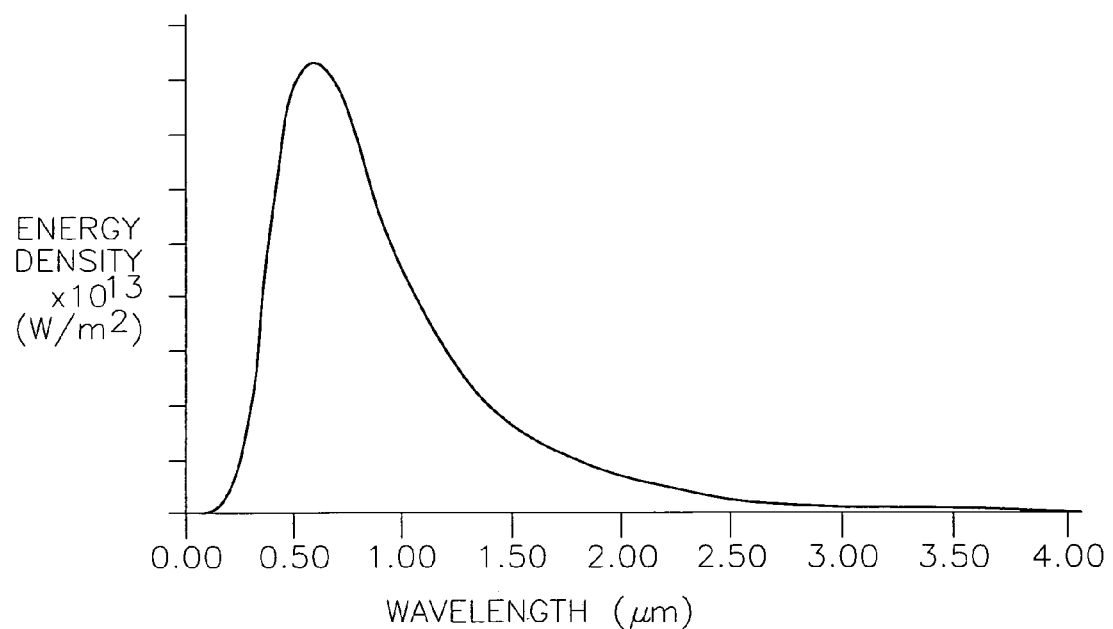
FIG. 1 is a theoretical black body radiation curve for 5000K.
Figure 2:
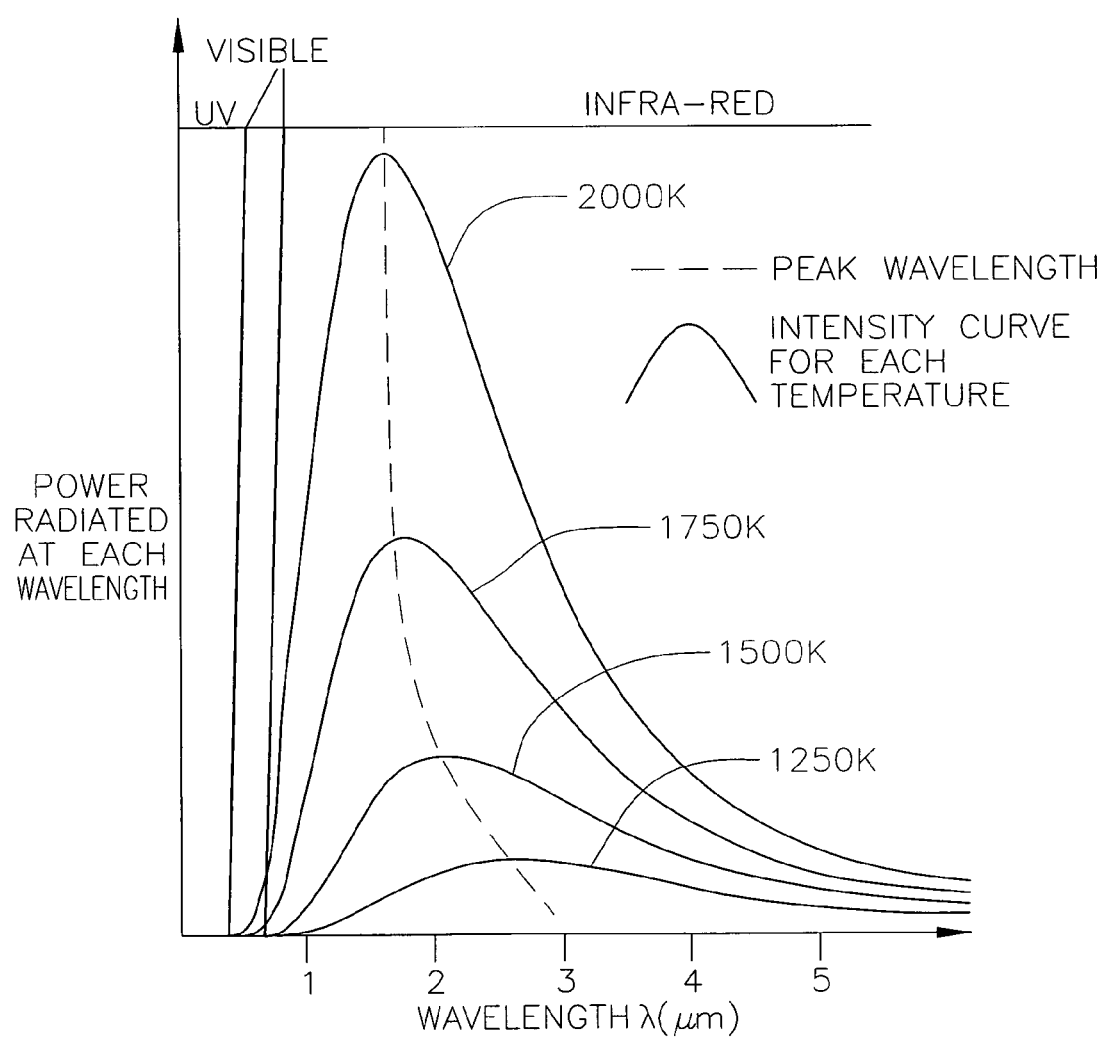
FIG. 2 are black body radiation curves with different peak wavelengths at different temperatures.

To energize the tip electrode 27 for RF ablation, the lead wire 40 is anchored in the plug 44. With reference to FIGS. 1, 2A and 5, the lead wire 40 extends through the second lumen 32 of intermediate section 14, the central lumen 18 of the catheter body 12, and the control handle 16, and terminates at its proximal end in an input jack (not shown) that may be plugged into an appropriate monitor (not shown). The portion of the lead wire 40 extending through the central lumen 18 of the catheter body 12, control handle 16 and distal end of the intermediate section 14 is enclosed within a protective sheath 52, which can be made of any suitable material, preferably Teflon™. The protective sheath 52 is anchored at its distal end to the distal end of the intermediate section 14 by gluing it in the lumen 32 with polyurethane glue or the like. The lead wire 40 is attached to the tip electrode 27 by any conventional technique. In the illustrated embodiment, connection of the lead wire 40 to the tip electrode 27 is accomplished, for example, by welding the distal end of the lead wire 40 into the blind hole 102 (FIGS. 9 and 7B) in the plug 44 of the tip electrode 27.

Figure 9:
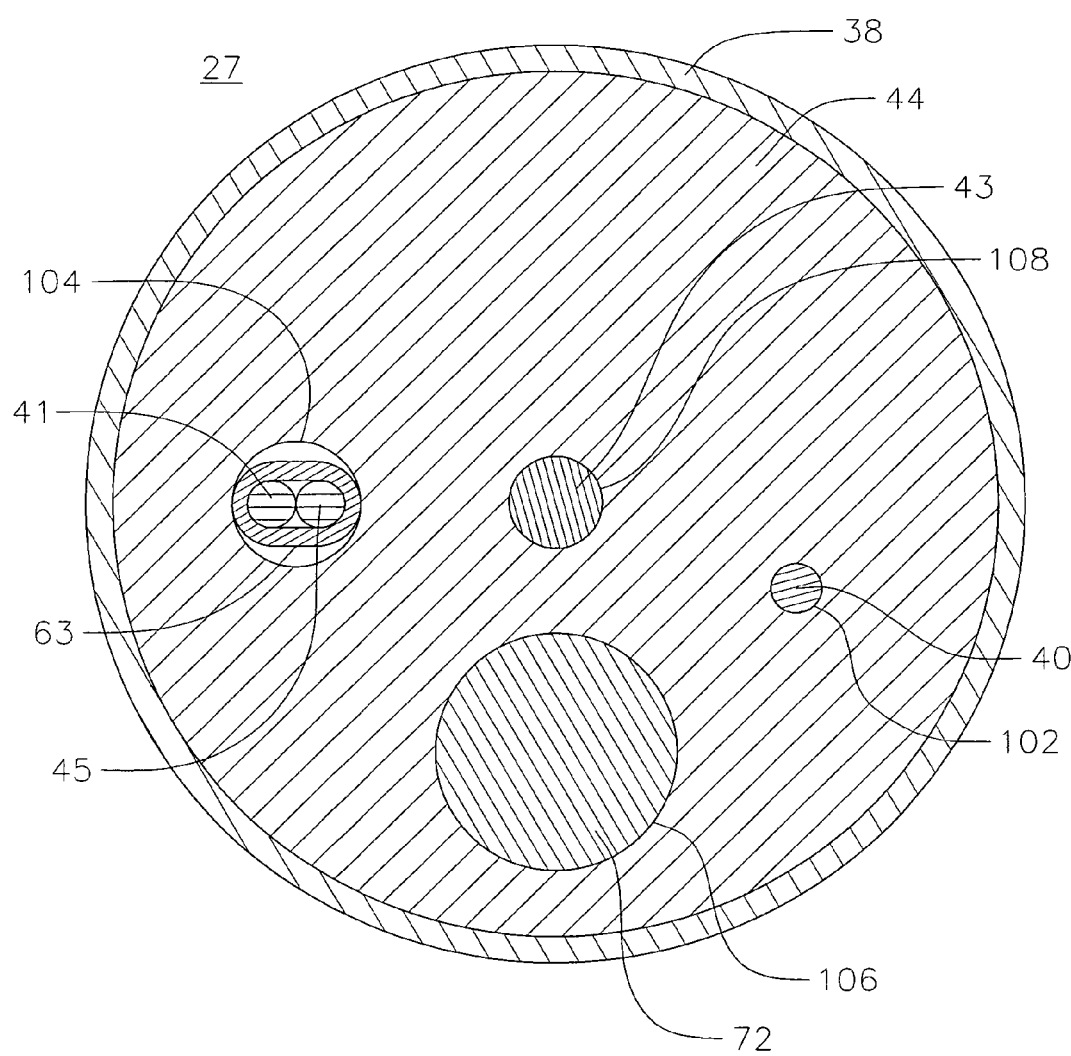
FIG. 9 is a longitudinal cross-sectional view of an embodiment of the tip electrode of FIGS. 7A and 7B, taken along line 9-9.

A temperature sensing means is provided for the tip electrode 27 in the disclosed embodiment. Any conventional temperature sensing means, e.g., a thermocouple or thermistor, may be used. With reference to FIGS. 5B and 7B, a suitable temperature sensing means for the tip electrode 27 comprises a thermocouple formed by a wire pair that is embedded a few millimeters proximal the distal tip of the catheter. One wire of the wire pair is the copper wire 41, e.g., a number 40 copper wire. The other wire of the wire pair is the constantan wire 45, which gives support and strength to the wire pair. The wires 41 and 45 of the wire pair are electrically isolated from each other except at their distal ends where they contact and are twisted together, covered with a short piece of plastic tubing 63, e.g., polyimide, and covered with epoxy. The plastic tubing 63 is then attached in the hole 104 of the plug 44, by epoxy or the like (FIG. 9). The wires 41 and 45 extend through the second lumen 32 in the intermediate section 14. Within the catheter body 12 the wires 41 and 45 extend through the central lumen 18 within the protective sheath 52 along with the lead wires 40. The wires 41 and 45 then extend out through the control handle 16 and to a connector (not shown) connectable to a temperature monitor (not shown). Alternatively, the temperature sensing means may be a thermistor. A suitable thermistor for use in the present invention is Model No. AB6N2-GC14KA143T/37C sold by Thermometrics (New Jersey). Moreover, suitable catheter designs with temperature sensing in the form of microfabricated thin film assembly of which one layer is a sensor layer of thermoresistive material include those described in U.S. application Ser. No. 11/280,759 entitled Catheter With Multiple Microfabricated Temperature Sensors, filed Nov. 15, 2005, and U.S. Ser. No. 11/281,203 entitled Catheter With Microfabricated Temperature Sensing, filed Nov. 15, 2005, the entire disclosures of which are hereby incorporated by reference.

The embodiment of the catheter disclosed herein is unideflectional, having a single puller wire; however, it is understood by one of ordinary skill in the art that the catheter may be bi-directional with two puller wires. Referring to FIGS. 5B and 7B, the puller wire 42 for deflecting the intermediate section 14 extends through the catheter body 12 and is anchored at its proximal end to the control handle 16. The puller wire is made of any suitable metal, such as stainless steel or Nitinol, and is preferably coated with Teflon™ or the like. The coating imparts lubricity to the puller wire. The puller wire preferably has a diameter ranging from about 0.006 to about 0.010 inches. A compression coil 56 is situated within the catheter body 12 in surrounding relation to the puller wire. The compression coil 56 extends from the proximal end of the catheter body 12 to the proximal end of the intermediate section 14. The compression coil is made of any suitable metal, preferably stainless steel, and is tightly wound on itself to provide flexibility, i.e., bending, but to resist compression. The inner diameter of the compression coil is preferably slightly larger than the diameter of the puller wire 42. The Teflon™ coating on the puller wire allows it to slide freely within the compression coil. If desired, particularly if the lead wire 40 is not enclosed by the protective sheath 52, the outer surface of the compression coils can be covered by a flexible, non-conductive sheath, e.g., made of polyimide tubing, to prevent contact between the compression coils and any other wires within the catheter body 12.

The compression coil 56 is anchored at its proximal end to the proximal end of the stiffening tube 20 in the catheter body 12 by glue joint 50 and at its distal end to the intermediate section 14 by glue joint (not shown). Both glue joints preferably comprise polyurethane glue or the like. The glue may be applied by means of a syringe or the like through a hole made between the outer surface of the catheter body 12 and the central lumen 18. Such a hole may be formed, for example, by a needle or the like that punctures the outer wall 22 of the catheter body 12 and the stiffening tube 20 which is heated sufficiently to form a permanent hole. The glue is then introduced through the hole to the outer surface of the compression coil 56 and wicks around the outer circumference to form a glue joint about the entire circumference of the compression coil.

With reference to FIGS. 5B and 6, the puller wire 42 extends into the first lumen 30 of the intermediate section 14. In the illustrated embodiment of FIG. 8B, the distal end of the puller wire 42 is anchored to the distal end side wall of the first lumen 30 of the tubing 19 of the intermediate section 14. The distal end of the puller wire 42 is anchored by means of a T-bar anchor 109 created by a metal tube 120, e.g., a short segment of hypodermic stock, that is fixedly attached, e.g. by crimping, to the distal end of the puller wire 42. The tube has a section that extends a short distance beyond the distal end of the puller wire 42. A cross-piece 121 made of a small section of stainless steel ribbon or the like is soldered or welded in a transverse arrangement to the distal end of the metal tube which is flattened during the operation. A notch is created in the side wall of tubing 19 resulting in an opening in the lumen 30 carrying the puller wire 42. The cross piece 121 lies transversely within the notch. Because the length of the ribbon forming the cross-piece 121 is longer than the diameter of the opening into the lumen 30, the anchor 109 cannot be pulled completely into the lumen 30. The notch is then sealed with polyurethane glue 122 or the like to give a smooth outer surface. The glue flows into the lumen 30 to fully secure the anchor. A t-bar anchor is described in U.S. Pat. No. 6,468,260, the entire disclosure of which is hereby incorporated by reference. Other means for anchoring the distal end of the puller wire 42 would be recognized by those skilled in the art and are included within the scope of the invention. For example, another blind hole may be formed in the proximal surface of the plug 44 in which the metal tube 120 at the distal end of the puller wire may be fixed by soldering. Anchoring the puller wire 42 within the tip electrode 27 provides additional support, reducing the likelihood that the tip electrode 27 will fall off. Within the first lumen 30 of the intermediate section 14, the puller wire 42 extends through a plastic, preferably Teflon™, sheath 81, which prevents the puller wire 42 from cutting into the wall of the intermediate section 14 when the intermediate section is deflected. Longitudinal movement of the puller wire 42 relative to the catheter body 12, which results in deflection of the tip section 36, is accomplished by suitable manipulation of the control handle 16. Suitable control handles are described in U.S. Pat. No. 6,602,242, the entire disclosure of which is hereby incorporated by reference.

Figure 4:
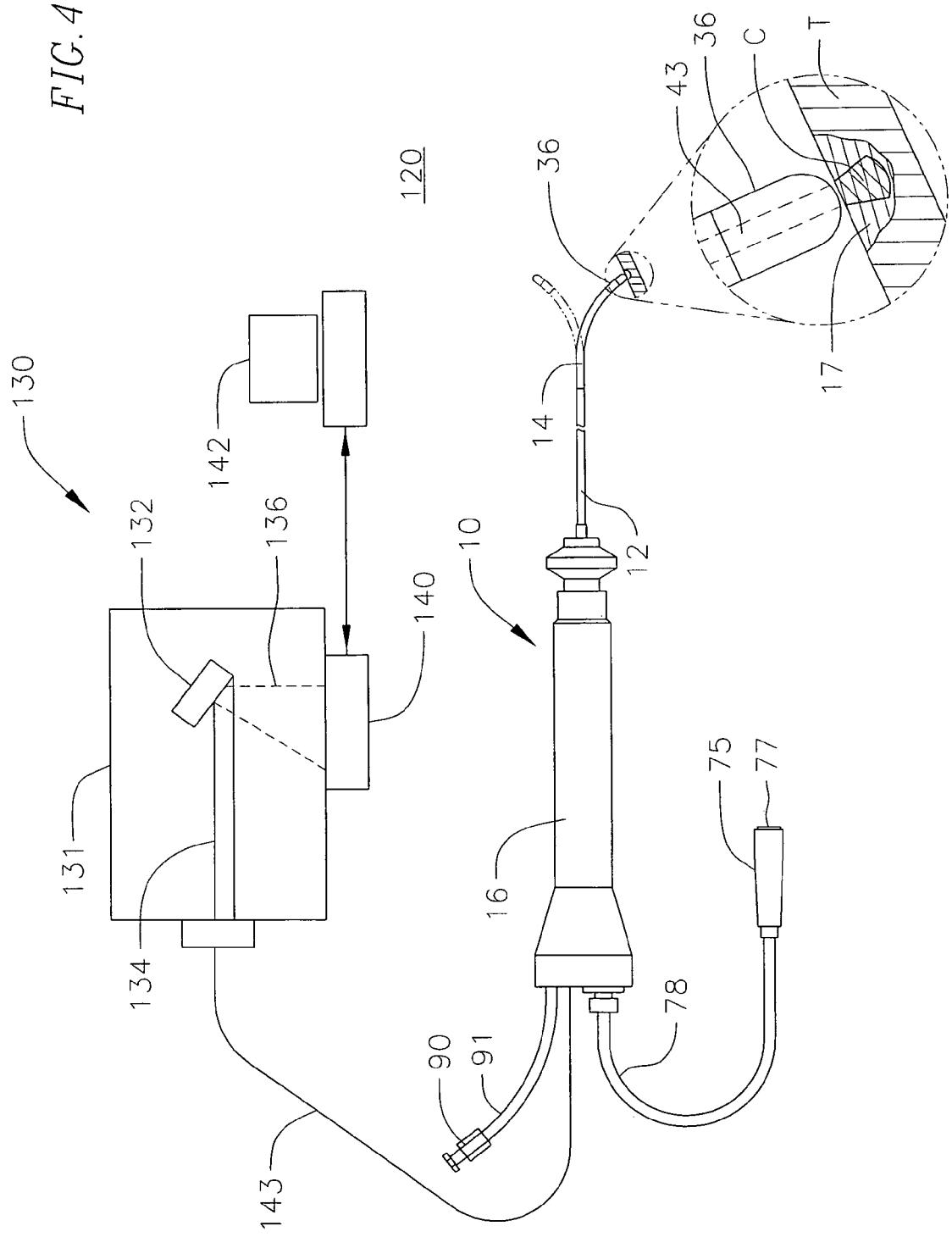
FIG. 4 illustrates another embodiment of the present invention for ablation and optical pyrometry in accordance with the present invention.

In the illustrated embodiment of FIGS. 7A and 8A, the tip section 36 carries an electromagnetic sensor 72, and as mentioned, the electromagnetic sensor may be carried in the plastic housing 21, with its distal end anchored in the blind hole 106 in the plug 44. The electromagnetic sensor 72 is connected to an electromagnetic sensor cable 74. As shown in FIGS. 5A and 6, the sensor cable 74 extends through the third lumen 34 of the tip section 36, through the central lumen 18 of the catheter body 12, and into the control handle 16. The electromagnetic sensor cable 74 then extends out the proximal end of the control handle 16 within an umbilical cord 78 (FIG. 4) to a sensor control module 75 that houses a circuit board (not shown). Alternatively, the circuit board can be housed within the control handle 16, for example, as described in U.S. patent application Ser. No. 08/924,616, entitled "Steerable Direct Myocardial Revascularization Catheter", the disclosure of which is incorporated herein by reference. The electromagnetic sensor cable 74 comprises multiple wires encased within a plastic covered sheath. In the sensor control module 75, the wires of the electromagnetic sensor cable 74 are connected to the circuit board. The circuit board amplifies the signal received from the electromagnetic sensor 72 and transmits it to a computer in a form understandable by the computer by means of the sensor connector 77 at the proximal end of the sensor control module 75, as shown in FIG. 4. Because the catheter can be designed for single use only, the circuit board may contain an EPROM chip which shuts down the circuit board approximately 24 hours after the catheter has been used. This prevents the catheter, or at least the electromagnetic sensor, from being used twice. Suitable electromagnetic sensors for use with the present invention are described, for example, in U.S. Pat. Nos. 5,558,091, 5,443, 489, 5,480,422, 5,546,951, 5,568,809, and 5,391,199 and International Publication No. WO 95/02995, the disclosures of which are incorporated herein by reference. An electromagnetic mapping sensor 72 may have a length of from about 6 mm to about 7 mm and a diameter of about 1.3 mm.

In operation, the catheter tip electrode 27 is energized for ablation with the tissue in contact with the tip electrode. As a lesion forms in the tissue from ablation carried out by tip electrode 27 of the catheter 10 (or by another catheter), the tissue heats up due to resistive heating and emits black body radiation which is collected by the fiber optic 43 for delivery to the optical processing system which quantifies the amount of black body radiation emitted at a particular wavelength region(s). Such black body tissue temperature reading by the present invention allows a noninvasive determination of tissue temperature not only at depths below tissue surface but also at the tissue surface. As understood by one of ordinary skill in the art, the black body radiation of the tissue can be detected at a number of wavelengths in the near, mid and far infrared regions of the optical spectrum. Thus, the optical detection system can be configured to detect such different wavelengths for different applications and uses, as desired or appropriate. In that regard, the optical detection system could contain a number of optical detectors, such as CCD, PMT, photodiode, or other similar technology. In any case, the pyrometric temperature sensing capability of the catheter tip during ablation and lesion formation is intended to prevent critical thresholds in temperature associated with such events as steam pop, thrombus formation, char, etc. The simplicity of the present invention allows the pyrometric temperature sensing to be accomplished in a variety of catheter configurations, including needle ablation and injection catheters, irrigated and non-irrigated catheters, as well as a multitude of catheter curve shapes.

Figure 10:
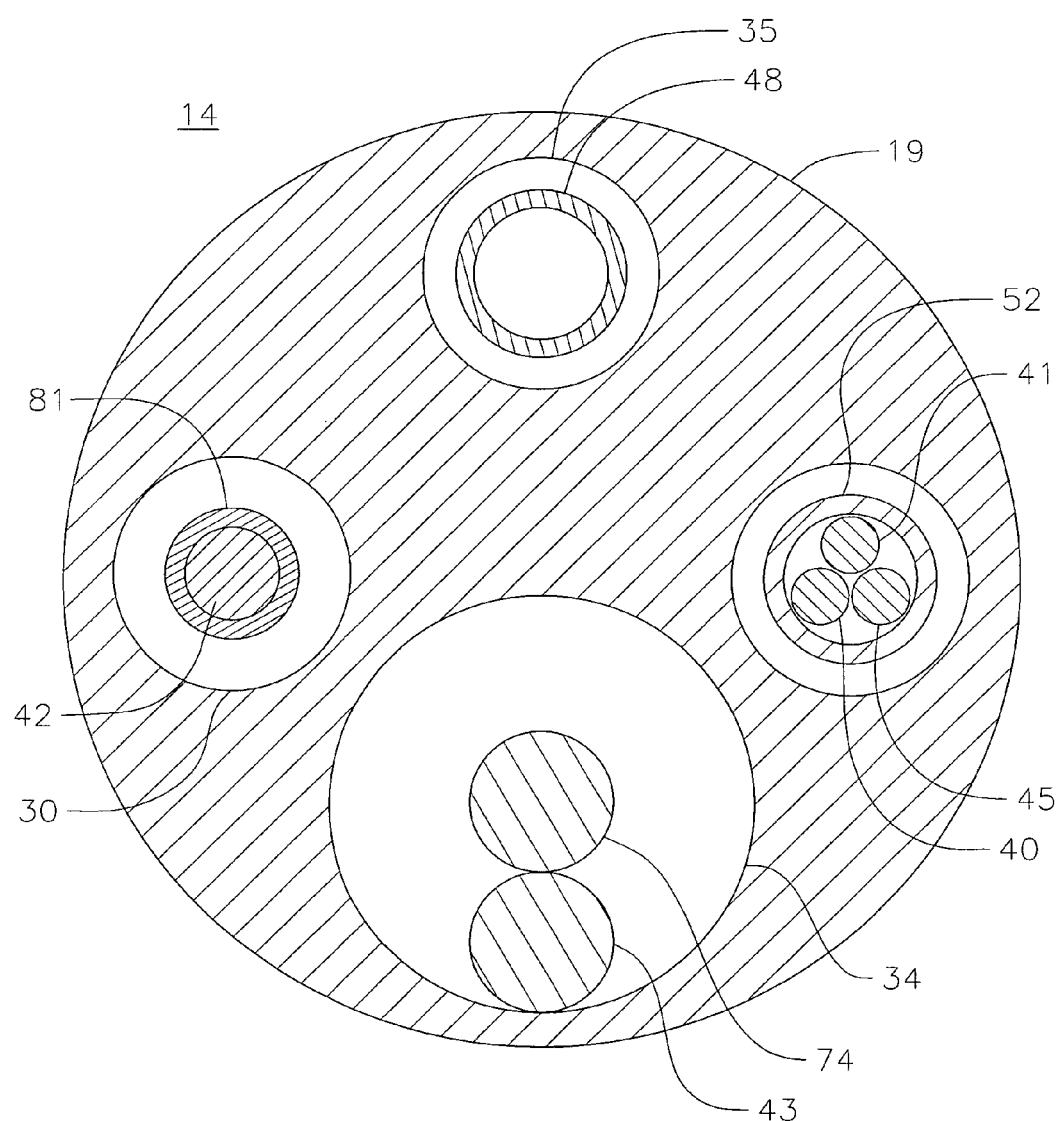
FIG. 10 is a longitudinal cross-sectional view of an intermediate section of another embodiment of a catheter configured for irrigation in accordance with the present invention.
Figure 11:
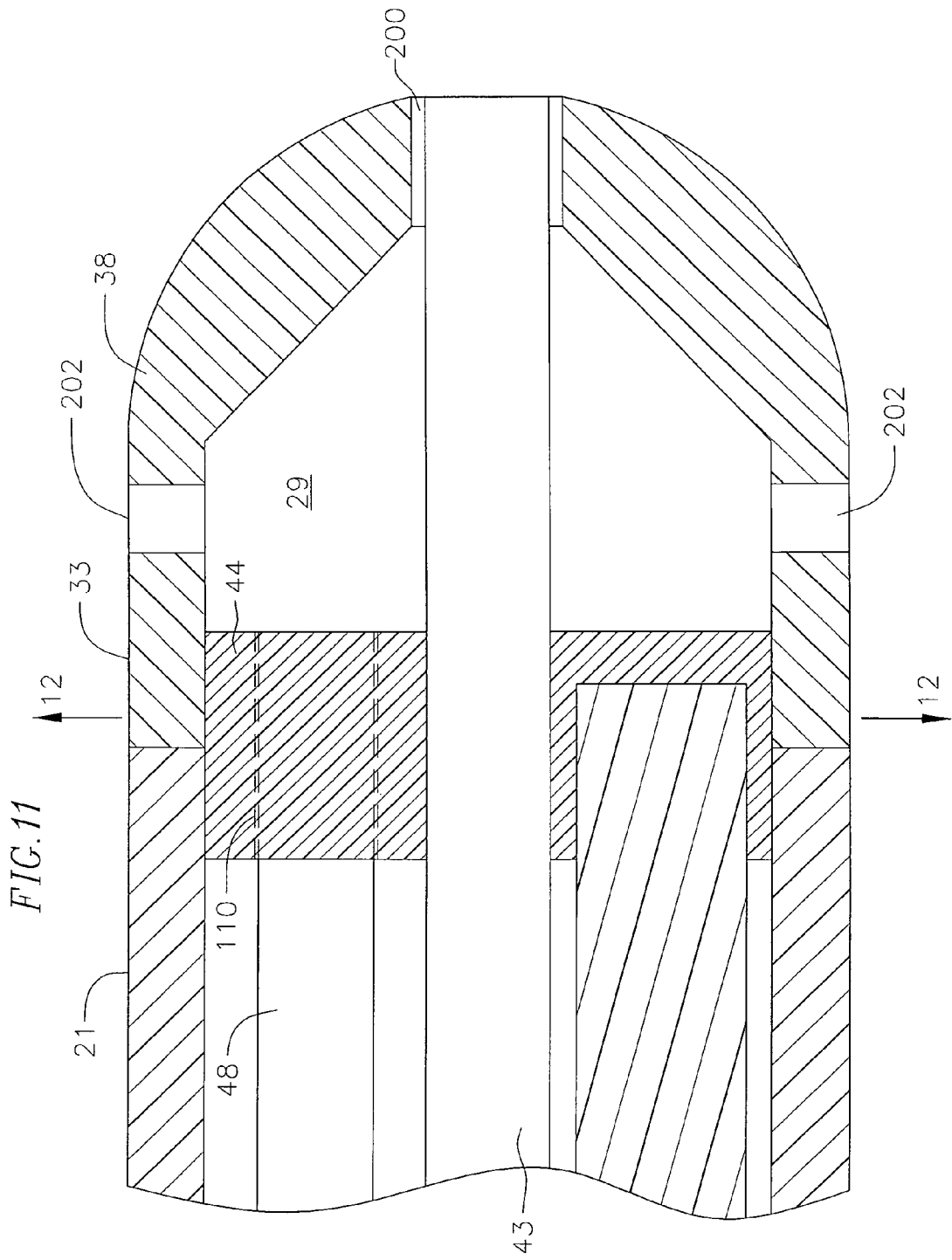
FIG. 11 is a side cross-sectional view of the embodiment of the catheter configured for irrigation according to the present invention, including the junction between a tip electrode and a plastic housing.
Figure 12:
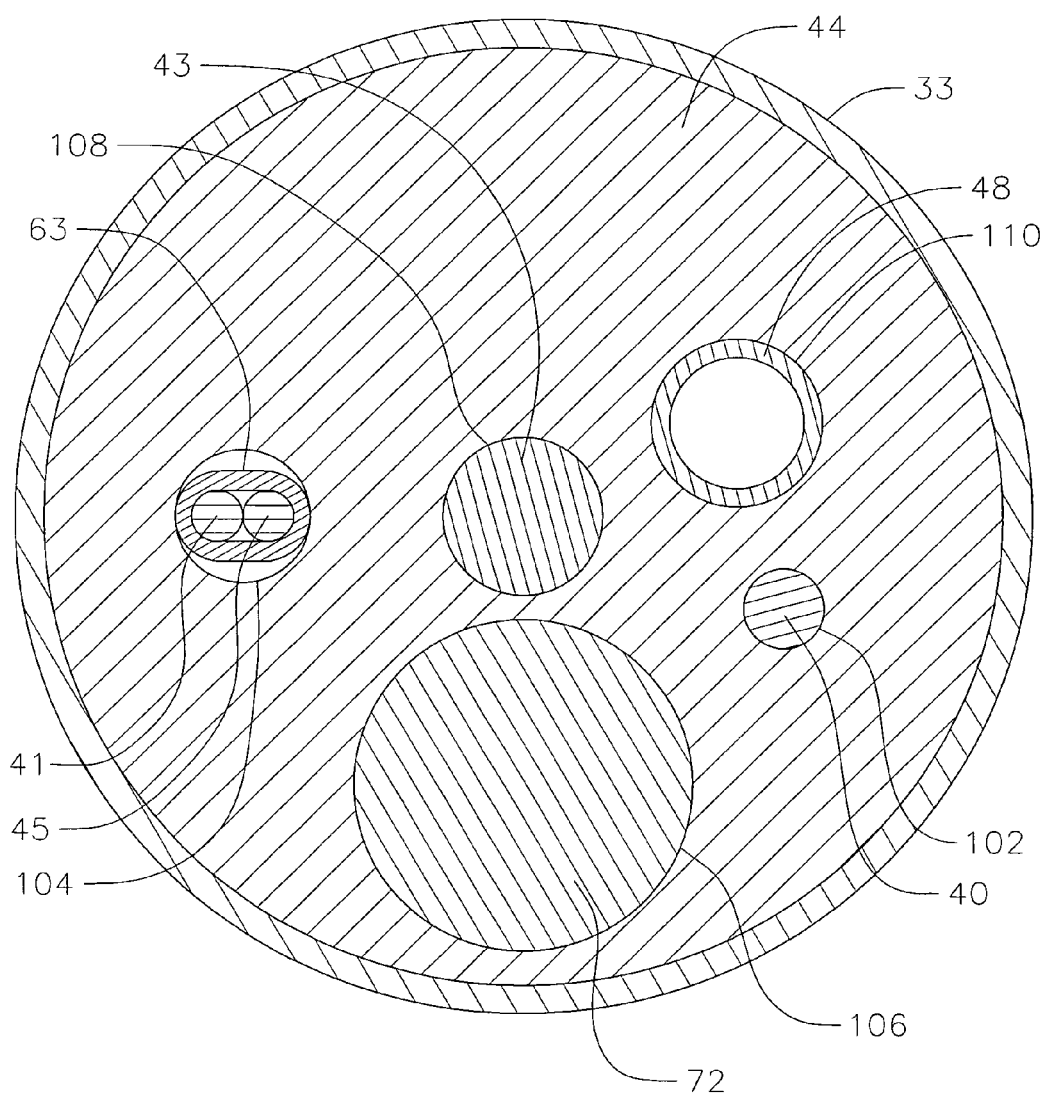
FIG. 12 is a longitudinal cross-sectional view of the tip electrode of FIG. 11, taken along line 12-12.

Illustrated in FIGS. 10, 11 and 12 is an embodiment of a catheter adapted for pyrometric temperature sensing and irrigation at the tip electrode with fluid, e.g., saline, that is fed into a hollow cavity 29 formed by the shell and plug by an irrigation tube 48. In this embodiment, the electromagnetic sensor cable 74 extends through the lumen 34 along with the optical fiber 43. The irrigation tube 48 extends through the central lumen 18 of the catheter body 12, the fourth lumen 35 of the intermediate section 14 (FIG. 10), through the plastic housing 21 and passage 110 in the plug 44 (FIG. 12). The tube 48 is anchored in the passage 110 and in the fourth lumen 35 by polyurethane glue or the like. The proximal portion of the tube 48 extends through the control handle 16 and terminates in a luer hub 90 (FIG. 4) or the like at a location proximal to the control handle. In the disclosed embodiment, the irrigation tube 48 transitions from a smaller diameter at the distal end to a larger diameter at the proximal end. For example, a distal segment can be about 0.0155×0.0175 inches and a proximal segment can be about 0.024×0.28 inches. In practice, fluid may be injected by a pump (not shown) into the irrigation tube 48 through the luer hub 90, and into the hollow cavity 29 in the tip electrode 27, and out irrigation openings 22 formed in the shell 38. In this embodiment, the collection opening 200 may larger than the circumference of the optical fiber 43 so that fluid can also seep around the distal end of the optical fiber and out the distal end of the tip electrode. The infusion tube 48 may be made of any suitable material, and is preferably made of polyimide tubing.

In accordance with a feature of the present invention, a pump (not shown) maintains the fluid at a positive pressure differential relative to outside the hollow cavity 29 so as to provide a constant unimpeded flow or seepage of fluid outwardly from the hollow cavity 29 through the collection openings for a variety of functions, such as cleaning the distal tip of the optical fiber 43 and/or cooling the tip electrode and/or the ablation site and increasing conduction for deeper and larger lesions.

The preceding description has been presented with reference to presently preferred embodiments of the invention. Workers skilled in the art and technology to which this invention pertains will appreciate that alterations and changes in the described structure may be practiced without meaningfully departing from the principal, spirit and scope of this invention.

Accordingly, the foregoing description should not be read as pertaining only to the precise structures described and illustrated in the accompanying drawings, but rather should be read consistent with and as support to the following claims which are to have their fullest and fair scope.

What is claimed is:

1. A catheter, comprising:
 a catheter body;
 a tip section distal the catheter body, the tip section comprising:
  an ablation electrode configured to ablate tissue, the ablation electrode comprising a shell and a plug defining a generally hollow cavity, and
  a separate optical fiber passing through the generally hollow cavity and having a distal end received in an opening formed in the shell of the ablation electrode, the optical fiber configured to detect black body radiation from the tissue during tissue ablation through a distal face of the optical fiber.

2. A system for detecting black body radiation during tissue ablation, comprising:
 a catheter comprising:
  an ablation electrode comprising a shell and a plug defining a generally hollow cavity, and
  a separate optical collector passing through the generally hollow cavity and having a distal end received in an opening formed in the shell of the ablation electrode, the optical collector being adapted to collect black body radiation from tissue during tissue ablation through a distal face of the optical collector;
 an ablation energy source adapted to deliver ablation energy to the ablation element; and
 an optical detector adapted to detect the black body radiation at a selected wavelength region.

3. A system for ablation and tissue temperature measurement, comprising:
 a catheter comprising:
  an ablation element comprising a shell and a plug defining a generally hollow cavity, and
  a separate optical collector adapted to collect black body radiation from ablated tissue through a distal face of the optical collector, the separate optical collector passing through the generally hollow cavity and having a distal end received in an opening in the shell of the ablation element;
 an optical detection system having a wavelength selector, a quantification apparatus to provide signals representative of a wavelength region of the black body radiation, and a processor to determine a temperature measurement from said signals.

4. A system of claim 3, wherein the optical collector comprises an optical fiber.

5. A system of claim 3, wherein the ablation element is adapted for RF ablation.

6. A system of claim 3, wherein the ablation element is adapted for microwave ablation.

7. A system of claim 3, wherein the ablation element is adapted for ultrasound ablation.

8. A system of claim 3, wherein the ablation element is adapted for laser ablation.

9. A system of claim 3, wherein the ablation element is adapted for cryoablation.

10. A catheter for cardiac ablation, comprising:
   a catheter body;
   a deflectable portion distal the catheter body;
   a tip section comprising:
      a tip electrode adapted for RF ablation of cardiac tissue, the tip electrode comprising a shell and plug defining a generally hollow cavity, and
      a separate optical collector passing through the generally hollow cavity and having a distal end received in an opening formed in the shell of the tip electrode, the optical collector being adapted to detect black body radiation from the cardiac tissue indicative of a temperature of the cardiac tissue during tissue ablation through a distal face of the optical collector.

11. A catheter of claim 10, wherein the optical collector is an optical fiber.

12. A catheter of claim 11, wherein the catheter further comprises a control handle, and the optical fiber extends through the catheter from the tip electrode to the control handle proximal the catheter body.

13. A catheter of claim 10, wherein the catheter body is configured for bi-directional deflection.

14. A catheter of claim 10, wherein the catheter is configured for irrigation.

15. A catheter of claim 10, wherein the shell has openings for fluid to flow outside the tip electrode.

16. A catheter of claim 10, wherein the tip section comprises an electromagnetic location sensor.

17. A system for cardiac ablation and tissue temperature measurement, comprising:
   a catheter comprising:
      a catheter body,
      a deflectable portion distal the catheter body, and
      a tip section, the tip section comprising:
         a tip electrode adapted for RF ablation of cardiac tissue, the tip electrode comprising a shell and a plug defining a generally hollow cavity, and
         a separate optical collector passing through the cavity and having a distal end received in an opening formed in the shell of the tip electrode to detect black body radiation from the cardiac tissue during tissue ablation through a distal face of the optical collector;
   an optical detection system in communication with the optical collector, the optical detector system being configured to process signals representative of a wavelength of at least a portion of the black body radiation to determine a tissue temperature.

18. A system of claim 17, wherein the detection system comprises a wavelength selector, a quantification apparatus to provide the signals and a processor to determine the tissue temperature based on the signals.

* * * * *